(12) United States Patent
Yamanaka

(10) Patent No.: US 8,697,758 B2
(45) Date of Patent: Apr. 15, 2014

(54) UREA COMPOUND, SELF-ASSEMBLY OF UREA COMPOUNDS, ORGANOGEL CONTAINING SELF-ASSEMBLY, AND METHOD FOR PRODUCING ORGANOGEL

(75) Inventor: Masamichi Yamanaka, Shizuoka (JP)

(73) Assignees: National University Corporation Shizuoka University, Shizuoka (JP); Nissan Chemical Industries, Ltd., Tokyo (JP)

( * ) Notice: Subject to any disclaimer, the term of this patent is extended or adjusted under 35 U.S.C. 154(b) by 487 days.

(21) Appl. No.: 13/120,388

(22) PCT Filed: Sep. 15, 2009

(86) PCT No.: PCT/JP2009/004606
§ 371 (c)(1),
(2), (4) Date: Mar. 22, 2011

(87) PCT Pub. No.: WO2010/035427
PCT Pub. Date: Apr. 1, 2010

(65) Prior Publication Data
US 2011/0198534 A1 Aug. 18, 2011

(30) Foreign Application Priority Data
Sep. 24, 2008 (JP) .................. 2008-244520

(51) Int. Cl.
B01J 13/00 (2006.01)
B01J 19/10 (2006.01)
C07C 275/36 (2006.01)
C07C 275/20 (2006.01)
C09K 3/00 (2006.01)
A61K 8/02 (2006.01)

(52) U.S. Cl.
USPC ... 516/99; 516/101; 252/182.12; 252/182.13; 564/32; 564/47; 564/48; 564/50; 564/52

(58) Field of Classification Search
USPC .............. 564/52, 47, 48, 32, 50; 516/99, 101; 252/182.12, 182.13
See application file for complete search history.

(56) References Cited

U.S. PATENT DOCUMENTS 3,567,781 A * 3/1971 Clark ................ 568/49

FOREIGN PATENT DOCUMENTS

| JP | 7247473 | 9/1995 |
| JP | 7247474 | 9/1995 |
| JP | 7247475 | 9/1995 |
| JP | 11021556 | 1/1999 |
| JP | 2000072736 | 3/2000 |
| JP | 2000126585 | 5/2000 |
| JP | 2000229992 | 8/2000 |
| JP | 2000239663 | 9/2000 |
| JP | 2000248258 | 9/2000 |
| JP | 2000256303 | 9/2000 |
| JP | 2002053840 | 2/2002 |
| JP | 2004182692 | 7/2004 |
| JP | 2004359643 | 12/2004 |
| JP | 2008189559 | 8/2008 |
| WO | 2010035427 A1 | 4/2010 |
| WO | WO 2012121394 A1 * | 9/2012 |

OTHER PUBLICATIONS

Maaike de Loos, et al, "Tripodal Tris-Urea Derivatives as Gelators for Organic Solvents", Eur. J. Org. Chem., (2000), 3675-3678.*
Machine Translation of Publ. No. JP 2008-189559, published Aug. 2008, Japan patent Office, Tokyo, Japan, obtained online @ http://dossier1.ipdl.inpit.go.jp/AIPN/odse_top_dn.ipdl?N0000=7400 (Downloaded Aug. 22, 2013).*
Machine Translation of Publ. No. JP 2004-359643, published Dec. 2004, Japan patent Office, Tokyo, Japan, obtained online @ http://dossier1.ipdl.inpit.go.jp/AIPN/odse_top_dn.ipdl?N0000=7400 (Downloaded Aug. 22, 2013).*
Derwent Abstract on EAST, week 201271, London: Derwent Publications Ltd., AN 2012-L94121, Class D13, WO 2012121394 A1, (Nissan Chem Ind Ltd), abstract, pp. 1-4.*
Mahalingam Vanjinathan et al., Syntheses, Characterization, Optical Properties, and Charge-Transfer Complexation Study of Fluorescent Poly(aryl-ether-urea) Dendrimers, Journal of Polymer Science: Part A: Polymer Chemistry, 2008, pp. 713-724, vol. 46, No. 2, (Publ. online Dec. 6, 2007).

(Continued)

*Primary Examiner* — Daniel S Metzmaier
(74) *Attorney, Agent, or Firm* — Wood, Herron & Evans, LLP

(57) ABSTRACT

A urea compound of the present invention is represented by general formula (I) shown below:

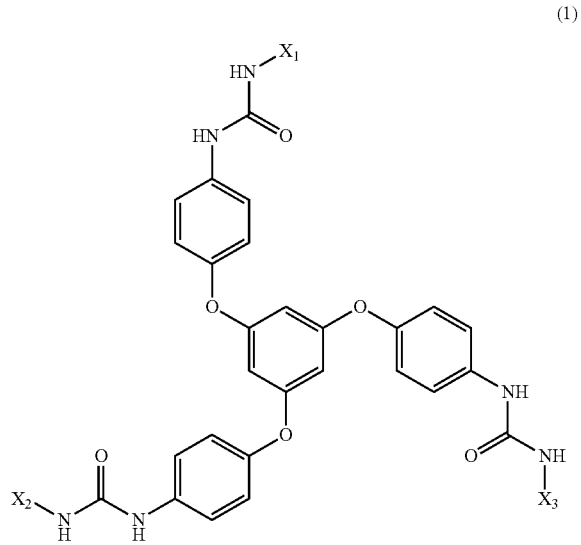

(I)

wherein each of $X_1$, $X_2$ and $X_3$ independently represents a hydrogen atom, an alkyl group or an aryl group. The aryl group may have one or more functional groups selected from the group consisting of halogen groups, alkyl groups and alkoxy groups.

15 Claims, 2 Drawing Sheets

(56) References Cited

OTHER PUBLICATIONS

Hong Yang et al., Switchable Fluorescent Organogels and Mesomorphic Superstructure Based on Naphthalene Derivatives, Langmuir, 2007, pp. 8224-8230, vol. 23, No. 15, (web publ. date Jun. 20, 2007).

Masamichi Yamanaka et al., Chloroalkane Gel Formations by Tris-urea Low Molecular Weight Gelator under Various Conditions, Journal of Organic Chemistry, 2009, pp. 5390-5394, vol. 74, No. 15, (web publ. date Jun. 24, 2009).

Masamichi Yamanaka et al., Synthesis and estimation of gelation ability of C3-symmetry tris-urea compounds, Tetrahedron, 2008, pp. 11558-11567, vol. 64, No. 51, (Publ. online Oct. 18, 2008).

Yamanaka, Masamichi, et al., "Reversible sol-gel transition of a tris-urea gelator that responds to chemical stimuli", Tetrahedron Letters, vol. 48, pp. 8990-8993, 2007 (web publ. date Oct. 22, 2007).

Office Action issued in related Chinese Application No. 200980137307.3, mailed on Feb. 20, 2013, with English translation of Search Report (12 pages).

* cited by examiner

UREA COMPOUND, SELF-ASSEMBLY OF UREA COMPOUNDS, ORGANOGEL CONTAINING SELF-ASSEMBLY, AND METHOD FOR PRODUCING ORGANOGEL

TECHNICAL FIELD

The present invention relates to a urea compound, a self-assembly of urea compounds, an organogel that includes a self-assembly, and a method for producing an organogel.

Priority is claimed on Japanese Patent Application No. 2008-244520, filed Sep. 24, 2008, the content of which is incorporated herein by reference.

BACKGROUND ART

Gels are structures containing a fluid, such as an organic solvent or water, within a three-dimensional network structure formed by a substance (gelator) that is capable of forming gels. A gel is referred to as an organogel when the fluid is an organic solvent and is referred to as a hydrogel when the fluid is water. Organogels have been used for adjusting the fluidity of cosmetics or coating materials in the fields of cosmetics, pharmaceuticals, agricultural chemicals, food products, adhesives, coating materials, resins, and the like. In addition, organogels have been widely used in the field of environmental conservation, for example, through the formation of solid matter by gelating the waste oil so as to prevent the water pollution or the like.

Studies on the gelators have been carried out mainly on the polymeric compounds. However, in recent years, research and development of low molecular compounds to which introduction of various functions is relatively easy compared to the polymeric compounds have been conducted. As mentioned above, organogels have been used in a wide range of fields, and further expansion in the fields of application therefor has also been expected in the future. For this reason, in the expansion of fields of application for the organogels, a low molecular weight compound serving as a gelator (hereafter, sometimes referred to as a low molecular weight gelator) is required to have a capacity to form gels in a wide variety of organic solvents. With respect to such challenges, a urea compound has been disclosed in the past, which is a low molecular weight gelator capable of forming highly stable gels when added in various organic solvents in small quantities (for example, refer to Patent Literatures 1 and 2).

Conventional low molecular weight gelators include a long chain alkyl group as in the urea compound described in Patent Literatures 1 and 2. In addition, the gelators have a structure with low symmetry. For this reason, it has not been easy to synthesize the derivatives thereof, and the functions of low molecular weight gelators have been difficult to predict. On the other hand, a highly symmetric urea compound having a benzene ring as a parent ring and includes no long chain alkyl group has been developed (for example, refer to Patent Literature 3). Since the urea compound described in Patent Document 3 is highly symmetric, a theoretical molecular design becomes possible.

CITATION LIST

Patent Literature

[Patent Literature 1]
Japanese Unexamined Patent Application, First Publication No. 2000-256303
[Patent Literature 2]
Japanese Unexamined Patent Application, First Publication No. 2004-359643
[Patent Literature 3]
Japanese Unexamined Patent Application, First Publication No. 2008-189559

SUMMARY OF INVENTION

Technical Problem

However, although the low molecular weight gelator described in Patent Literature 3 self-assembles and gelates in an organic solvent with relatively high polarity (such as acetone and ethanol) by forming a self-assembly, it was not suited for the gelation of non-polar organic solvents, such as toluene, or organic solvents with low polarity, such as dichloromethane. In addition, in the formation of organogels, gelators are required to gelate when added in smaller amounts. Further, new functions are required for the organogels.

In those cases where a variety of functions are given, the interaction with an inorganic salt is weak in the low molecular weight gelator of patent document 3, and as a result, the shape of the self-assembly that constitutes a gel cannot be controlled in accordance with the intended purpose, and thus all self-assemblies end up as fiber self-assemblies. The problem of gel production in accordance with the intended purpose has been left unresolved including the shape control of the self-assembly.

Accordingly, an object of the present invention is to obtain a urea compound that enables theoretical molecular design and can form a self-assembly and gelates a wide variety of organic solvents even if added in small amounts, an organogel that includes the urea compound and the production method thereof, and a self-assembly capable of providing various functions to the organogel.

Solution to Problem

The self-assembly process of the urea compound discovered in the present invention is promoted by adding an inorganic salt or an inorganic ion. As a result of intensive and extensive studies on the self-assembly process of the urea compound of the present invention, the present inventors discovered that the shape of the self-assembly of the urea compound can be controlled by the types of inorganic salt or inorganic ion to be added, to complete the following inventions.

A first aspect of the present invention is a urea compound represented by general formula (1) shown below.

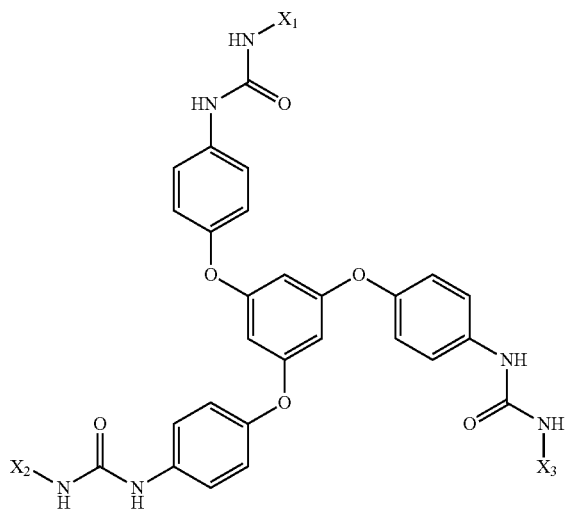

(1)

[Each of $X_1$, $X_2$ and $X_3$ independently represents a hydrogen atom, an alkyl group or an aryl group. The aryl group may have one or more functional groups selected from the group consisting of halogen groups, alkyl groups and alkoxy groups.]

In the first aspect of the present invention, it is preferable that each of $X_1$, $X_2$, and $X_3$ independently represent hydrogen, or a linear or branched alkyl group of 1 to 22 of carbon atoms.

In the first aspect of the present invention, it is characterized in that each of $X_1$, $X_2$, and $X_3$ independently represents a liner or branched alkyl group of 8 to 16 carbon atoms.

A second aspect of the present invention is a self-assembly which is formed by the self-assembling of the urea compound of the first aspect of the present invention.

In the second aspect of the present invention, it is preferable to include an inorganic salt or an inorganic ion.

In the second aspect of the present invention, it is preferable that the aforementioned inorganic salt be at least one kind of salt selected from the group consisting of an yttrium salt, a cesium salt, a lanthanum salt, a copper salt, a magnesium salt and an ytterbium salt.

In the second aspect of the present invention, it is preferable that the aforementioned inorganic ion be at least one kind of ion selected from the group consisting of an yttrium ion, a cesium ion, a lanthanum ion, a copper ion, a magnesium ion and an ytterbium ion.

A third aspect of the present invention is a particulate self-assembly which is formed by mixing the urea compound of the first aspect of the present invention with an yttrium salt, a cesium salt, an yttrium ion or a cesium ion.

A fourth aspect of the present invention is a fiber self-assembly which is formed by mixing the urea compound of the first aspect of the present invention with a copper salt, a lanthanum salt, a magnesium salt, an ytterbium salt, a copper ion, a lanthanum ion, a magnesium ion or an ytterbium ion.

A fifth aspect of the present invention is an organogel that contains the urea compound of the first aspect of the present invention and an organic solvent.

A sixth aspect of the present invention is an organogel that contains the self-assembly of the second aspect of the present invention and an organic solvent.

A seventh aspect of the present invention is an organogel that contains the particulate self-assembly of the third aspect of the present invention and an organic solvent.

An eighth aspect of the present invention is an organogel that contains the fiber self-assembly of the fourth aspect of the present invention and an organic solvent.

A ninth aspect of the present invention is a method for producing an organogel that includes a mixing step of mixing the urea compound of the first aspect of the present invention and an organic solvent to obtain a mixture, and an irradiation step of irradiating an ultrasonic wave onto the aforementioned mixture.

In the ninth aspect of the present invention, it is preferable that an inorganic salt or an inorganic ion be further mixed in the aforementioned mixing step.

Advantageous Effects of Invention

The urea compound of the present invention enables theoretical molecular design and can fowl a self-assembly and gelates a wide variety of organic solvents even if added in small amounts. In addition, the self-assembly of the present invention can provide various functions to organogels.

DESCRIPTION OF EMBODIMENTS

Figure 1:
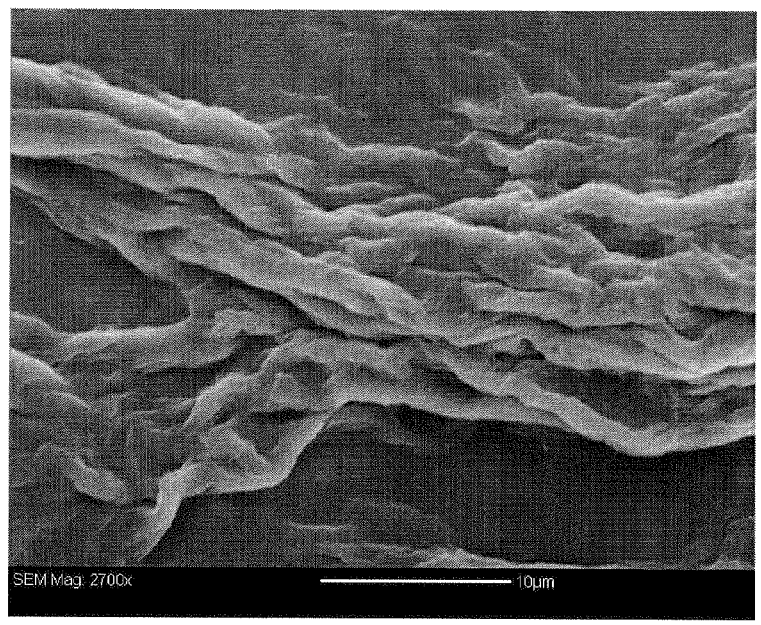
FIG. 1 is an SEM image of a gel obtained in Example 25.

[Urea Compound]
(Constitution)

The urea compound of the present invention is a urea compound represented by general formula (1) shown below (hereafter, referred to as a urea compound (1)). In formula (1), each of $X_1$, $X_2$ and $X_3$ independently represents a hydrogen atom, an alkyl group or an aryl group. The aryl group may have one or more functional groups selected from the group consisting of halogen groups, alkyl groups and alkoxy groups.

$X_1$, $X_2$, and $X_3$ can be selected, for example, in accordance with the shape of a desired self-assembly or the type of an organic solvent that constitutes an organogel.

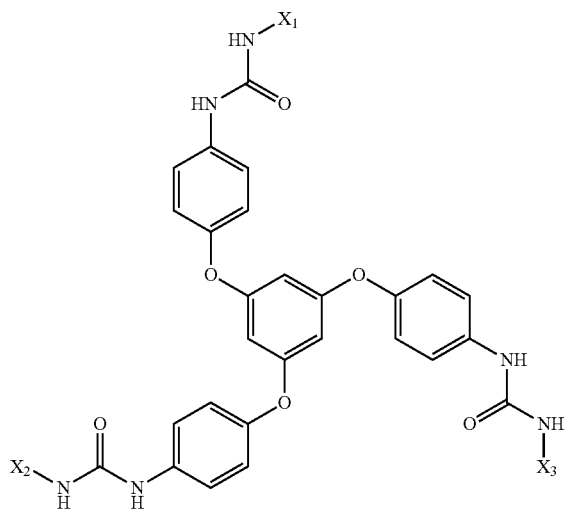

(1)

The number of carbon atoms of the alkyl group for $X_1$, $X_2$ and $X_3$ is not particularly limited, and can be determined depending on the type of organic solvent that constitutes an organogel. For example, a linear or branched alkyl group of 1 to 22 carbon atoms is preferable, and a linear alkyl group of 8 to 16 carbon atoms is more preferable from the viewpoint of gelating a wide variety of organic solvents. When the number of carbon atoms of the alkyl group is large, compatibility with an organic solvent of low polarity tends to increase, whereas when the number of carbon atoms of the alkyl group is small, compatibility with an organic solvent of high polarity tends to increase. Examples of the alkyl group for $X_1$, $X_2$ and $X_3$ include a methyl group, an ethyl group, a propyl group, an isopropyl group, an n-butyl group, an isobutyl group, a tert-butyl group, a pentyl group, an isopentyl group, a neopentyl group, an n-hexyl group, an n-heptyl group, an n-octyl group, an n-nonyl group, an n-decyl group, an n-undecyl group, an n-dodecyl group, an n-tridecyl group, an n-tetradecyl group, an n-pentadecyl group and an n-hexadecyl group.

The aryl group for $X_1$, $X_2$, and $X_3$ is not particularly limited. For example, some or all of the hydrogen atoms thereof may or may not be substituted with one or more functional groups selected from the group consisting of halogen groups, alkyl groups and alkoxy groups. Examples of the aryl group for $X_1$, $X_2$ and $X_3$ include a phenyl group, a naphthyl group and a biphenyl group.

The halogen group with which hydrogen atoms of the aryl group may be substituted is not particularly limited, and examples thereof include fluorine, chlorine, bromine, and iodine.

The alkyl group or alkoxy group with which hydrogen atoms of the aryl group may be substituted is not particularly limited and can be determined in accordance with the type of an organic solvent that constitutes an organogel. Examples of the alkyl group or alkoxy group with which hydrogen atoms of the aryl group may be substituted include an alkyl group or alkoxy group of 1 to 22 carbon atoms.

(Production Method)

A urea compound (1) can be produced, for example, in the following manner. First of all, by using phloroglucin as a starting material, a nitro-form is synthesized by introducing nitrophenol into the 1st, 3rd, and 5th positions thereof (first step). Subsequently, an amine form in which the nitro group of the nitro-form is converted to an amino group by the hydrogenation reaction is synthesized (second step). Then, a urea group is introduced thereto by the reaction with cyanic acid (CHNO), alkyl isocyanate or aryl isocyanate (hereafter, these three types of compounds are sometimes collectively referred to as isocyanate) (third step), to thereby produce the urea compound (1).

In the first step, for example, a first dispersion is prepared by suspending phloroglucin serving as a starting material, an alkali catalyst, and 4-fluoronitrobenzene in a first dispersion medium to carry out a reaction of substituting the hydroxyl group of phloroglucin with nitrophenol. Thereafter, the alkali catalyst is removed by filtering the first dispersion, and the first reaction medium is evaporated by distillation under reduced pressure. The obtained residue following the distillation under reduced pressure is dissolved in a collection medium for recovery. Further, after washing (washing treatment) with an aqueous solvent, the collection medium is once again evaporated by distillation under reduced pressure to obtain a solid, crude nitro-form. The obtained crude nitro-form is subjected to a purification treatment to obtain a nitro-form.

The alkali catalyst in the first step is not particularly limited, and examples thereof include potassium carbonate ($K_2CO_3$) and sodium carbonate ($Na_2CO_3$). Various organic liquids can be used as the first dispersion, and examples thereof include N,N-dimethylformamide (DMF). Various organic liquids can be used as the collection medium as long as they are capable of dissolving the nitro-form obtained in the first step, and examples thereof include dichloromethane.

Although the concentration of phloroglucin in the first dispersion is not particularly limited, for example, it is preferable to determine within the range from 10 to 200 mmol/L. The concentration of 4-fluoronitrobenzene in the first dispersion can be determined in accordance with the concentration of phloroglucin, and for example, a range between 30 and 800 mmol/L is preferred. The concentration of alkali catalyst in the first dispersion may be adequate as long as it is a satisfactory concentration for the introduction of nitrophenol into phloroglucin, and for example, it is preferable to determine within the range from 100 to 4.000 mmol/L.

The reaction in the first step is carried out, for example, by heating the first dispersion while stirring. Although the heating temperature is not particularly limited, for example, it is preferable to carry out the reaction within the range from 80 to 120° C. This is because the reaction proceeds poorly when the temperature is too low, whereas byproducts may be formed when the temperature is too high. The reaction time can be determined by taking the reaction temperature into consideration, and for example, it is preferable to determine within the range from 12 to 36 hours.

A known technique can be adopted for the washing treatment using an aqueous solvent. For example, a method may be employed, in which the residue recovered by dissolving in the collection medium and water are added and shaken in a separatory funnel, followed by the removal of an aqueous phase, and the saturated saline is then added to the separatory funnel and shaken, followed by the removal of an aqueous phase.

The method for purification treatment is not particularly limited, and examples thereof include silica gel chromatography, adsorption of impurities using activated clay, alumina, or the like, and recrystallization using an organic liquid.

In the second step, for example, a second dispersion prepared by suspending the nitro-form obtained in the first step and a hydrogenation catalyst in a second dispersion medium is stirred under a hydrogen atmosphere, and the nitro group is converted to an amino group by hydrogenation. Thereafter, the hydrogenation catalyst is removed by filtering the second dispersion. Then, the filtrate is concentrated to yield a crude amine-form, and an amine-form is obtained by subjecting the crude amine-form to a purification treatment.

The second dispersion medium can be selected in consideration of the solubility of the nitro-form obtained in the first step. Examples thereof include alcohols, such as ethanol and methanol, and ethyl acetate (EtOAc). Of these, it is preferable to use EtOAc.

Any hydrogenation catalyst may be used as long as it is capable of converting nitro group of the nitro-form obtained in the first step into an amino group by the hydrogenation reaction. Examples thereof include metal palladium (Pd), platinum (Pt), iron (Fe), nickel (Ni) and palladium carbon (Pd/C).

Although the concentration of nitro-form in the second dispersion is not particularly limited, for example, it is preferable to determine within the range from 10 to 200 mmol/L. The amount of hydrogenation catalyst added in the second dispersion may be adequate as long as it is a satisfactory amount for the hydrogenation reaction of nitro groups, and for example, it is preferable to determine within the range from 1 to 30% by mass with respect to the mass of the nitro-form.

In terms of the hydrogenation reaction time, the hydrogenation reaction of nitro groups proceeds poorly when the reaction time is too short, whereas the hydrogenation reaction becomes saturated and the time required for production is prolonged when the reaction time is too long, which is undesirable. Therefore, for example, it is preferable to determine the reaction time in the second step within the range from 5 to 30 hours.

In the third step, for example, a third dispersion is prepared by dissolving the amine-form obtained in the second step and isocyanate in a third reaction medium, and the third dispersion is allowed to react while stirring for an arbitrary time. The precipitated solid is filtered, and the urea compound (1) can be obtained by further washing the solid with a washing medium.

The type of isocyanate can be selected in accordance with the type of group introduced into $X_1$, $X_2$, and $X_3$ in the urea compound (1) represented by the aforementioned formula (1). For example, cyanic acid is selected when introducing hydrogen atoms, an alkyl isocyanate is selected when introducing alkyl groups, and an aryl isocyanate is selected when introducing aryl groups, into $X_1$, $X_2$, and $X_3$. Examples of alkyl isocyanates include methyl isocyanate, ethyl isocyanate, propyl isocyanate, butyl isocyanate, pentyl isocyanate, heptyl isocyanate, octyl isocyanate, nonyl isocyanate and decyl isocyanate. Examples of aryl isocyanates include phenyl isocyanate, tolyl isocyanate and naphthyl isocyanate.

It should be noted that in the third step, a urea group can be introduced by adding amines and triphosgene to the third reaction medium instead of the aforementioned isocyanate and allowing them to react.

The concentration of amine-form in the third dispersion is not particularly limited, and for example, it is preferable to determine within the range from 10 to 200 mmol/L. The concentration of isocyanate in the third dispersion can be determined in accordance with the concentration of amine-form, and for example, it is preferable to determine within the range from 30 to 800 mmol/L.

It is preferable to determine the third reaction medium by considering the solubility and the reaction temperature of the amine-form and isocyanate, and examples thereof include 1,2-dichloroethane with a relatively high boiling point. It is preferable that the washing medium be a medium that hardly dissolves the urea compound (1) and also readily dissolves unreacted amine-form and isocyanate. Examples thereof include organic liquids with relatively low polarity, such as hexane and dichloromethane.

The reaction method in the third step can be selected by taking the reactivity of amine-form and isocyanate into consideration, and examples thereof include mixing and stirring, heating and refluxing, and a combination of these processes.

The reaction temperature in the third step can be determined by taking the type of isocyanate added into consideration, and for example, it is preferable to determine within the range from room temperature to 80° C. This is because the above-mentioned range enables sufficient introduction of urea group into the amine-form, thereby increasing the yield of the urea compound (1). The reaction time in the third step can be determined by taking the reaction temperature into consideration, and for example, it is preferable to determine within the range from 5 to 40 hours. In addition, it is also possible to cool the third dispersion and precipitate a solid after the above reaction.

[Self-Assembly]
(Constitution)

The self-assembly referred to in the present invention is a self-assembly of the urea compound (1) due to the molecular interactions, which is formed into various higher-order structures such as a fiber self-assembly, a particulate self-assembly and a tubular self-assembly.

It is thought that the self-assembly of the present invention forms, for example, a fiber self-assembly, since the hydrogen atom and oxygen atom in a urea group form hydrogen bonds with the hydrogen atom or oxygen atom in another urea group. Further, by including an inorganic salt or an inorganic ion, it can be assumed that the urea compound (1) forms various higher-order structures, such as a fiber self-assembly, a particulate self-assembly and a tubular self-assembly, due to the presence of inorganic ions in the bonds between the urea groups.

In addition to the urea compound (1), the self-assembly can include an inorganic salt or an inorganic ion. It is preferable to select the inorganic salt or the inorganic ion by taking the desired shape of the self-assembly and the type of an organic solvent into consideration. Examples of the inorganic ion include ions of alkali metals, such as lithium, sodium, potassium and cesium, ions of alkaline earth metals, such as magnesium and calcium, ions of lanthanoids, such as lanthanum and ytterbium, ions of actinoids, such as yttrium, a copper ion and a zinc ion.

Examples of the inorganic salt include an inorganic salt formed of a positive component (cation) constituted of the aforementioned inorganic ion and a negative component (anion) like ions of halogen, such as chlorine and bromine, inorganic acids, such as sulfuric acid and nitric acid, and organic acids, such as formic acid and acetic acid. Specific examples thereof include bismuth chloride ($BiCl_3$), copper chloride ($CuCl_2$), magnesium chloride ($MgCl_2$), zinc chloride ($ZnCl_2$), lanthanum chloride ($LaCl_3$), magnesium bromide ($MgBr_2$), copper (I) bromide (CuBr), copper (II) bromide ($CuBr_2$), cesium bromide (CsBr), sodium iodide (NaI), yttrium nitrate ($Y(NO_3)_3$), ytterbium trifluoromethanesulfonate ($Yb(Otf)_3$) and lanthanum trifluoromethanesulfonate ($La(Otf)_3$). The structure of the self-assembly can be controlled by adding such an inorganic salt or an inorganic ion.

For example, in order to obtain a fiber self-assembly, it is preferable to use a copper ion, a lanthanum ion, a magnesium ion, an ytterbium ion, or a salt thereof. Further, for example, in order to obtain a particulate self-assembly, it is preferable to use a cesium ion, an yttrium ion, or a salt thereof.

Note that one type of the inorganic salt or the inorganic ion may be used alone, or two or more types thereof may be used in combination.

(Production Method)

The self-assembly is formed, for example, by mixing the urea compound (1) and an organic solvent to obtain a mixture, and irradiating an ultrasonic wave onto the aforementioned mixture for gel or sol formation.

The organic solvent refers to an organic compound in a liquid form to be used for dissolving materials or in a solid form with a relatively low melting point. Among the organic solvents, although the melting point of a solid organic compound cannot be uniquely defined, the melting point is preferably 40° C. or less and more preferably 35° C. or less.

The organic solvent is not particularly limited, and examples thereof include aromatic compounds such as benzene, toluene, xylene and nitrobenzene, ketones such as acetone and cyclohexanone, ethers such as tetrahydrofuran and dioxane, halogen materials such as chloroform, carbon tertrachloride, chlorobenzene, dichloroethane and dichloromethane, highly polar compounds such as acetonitrile, mineral oils such as gasoline, kerosene, light oil and heavy oil, vegetable oils such as soybean oil, olive oil, cotton seed oil, rapeseed oil and corn oil, fish oils, and a mixture thereof.

The ratio of the urea compound (1) in the above-mentioned mixture with respect to the organic solvent can be determined in accordance with the type of organic solvent, and for example, the concentration of the urea compound (1) in the above-mentioned mixture is preferably within the range from 0.5 to 30 mmol/L, and more preferably within the range from 1 to 15 mmol/L. This is because the self-assembly can be formed satisfactorily if the ratio is within the above-mentioned range.

An inorganic salt or an inorganic ion can be further mixed with the aforementioned mixture. The ratio of inorganic salt or inorganic ion in the aforementioned mixture can be determined in accordance with the concentration of the urea compound (1), and for example, the ratio is preferably within the range from 0.5- to 5-fold molar equivalent, and more preferably within the range from 0.8- to 1.2-fold molar equivalent with respect to the urea compound (1) in the aforementioned mixture. This is because the shape of the self-assembly can be favorably controlled if the ratio is within the above-mentioned range. It should be noted that the molar equivalent refers to a value derived by dividing the number of moles of an inorganic salt or an inorganic ion with the number of moles of the urea compound (1).

As for the conditions for the ultrasonic irradiation, any ultrasonic intensity and processing time sufficient to enable the urea compound (1) to self-assemble may be used. For example, the rated output per unit area of the ultrasonic oscillator is preferably within the range from 0.2 to 0.5 W/cm$^2$, and more preferably within the range from 0.3 to 0.4 W/cm$^2$. The oscillation frequency of the ultrasonic oscillator is preferably within the range from 30 to 100 kHz, and more preferably within the range from 40 to 60 kHz. Further, the processing time is preferably from one minute to 24 hours, and more preferably from one hour to 12 hours.

[Organogel]

(Constitution)

The organogel of the present invention contains the urea compound (1) and an organic solvent.

An organic solvent that constitutes the organogel is the same as the organic solvent used for producing the self-assembly.

The organogel of the present invention may include a self-assembly and an organic solvent. As described above, the shape of the self-assembly of the present invention can be controlled by adding various inorganic salts or inorganic ions. This is because it is possible to provide various functions to the organogel by including the self-assembly whose shape is controlled.

(Production Method)

A method for producing an organogel includes a mixing step of mixing the urea compound (1) and an organic solvent to obtain a mixture, and an irradiation step of irradiating an ultrasonic wave onto the aforementioned mixture.

The mixing step is a step of mixing the urea compound (1) with an organic solvent. The ratio of the urea compound (1) in the above-mentioned mixture with respect to the organic solvent can be determined in accordance with the type of organic solvent, and for example, the concentration of the urea compound (1) in the above-mentioned mixture is preferably within the range from 0.5 to 30 mmol/L, and more preferably within the range from 1 to 15 mmol/L. This is because the organogel can be formed satisfactorily if the ratio is within the above-mentioned range.

In the mixing step, an inorganic salt or an inorganic ion can be further mixed. An inorganic salt or an inorganic ion used to produce the organogel is the same as the inorganic salt or the inorganic ion included in the self-assembly. The ratio of inorganic salt or inorganic ion in the aforementioned mixture can be determined in accordance with the concentration of the urea compound (1), and for example, the ratio is preferably within the range from 0.5- to 5-fold molar equivalent, and more preferably within the range from 0.8- to 1.2-fold molar equivalent with respect to the urea compound (1) in the aforementioned mixture. By mixing an inorganic salt or an inorganic ion within the above-mentioned range, the minimum concentration (minimum gelation concentration) of the urea compound (1) necessary for gelating various organic solvents can be reduced, and the shape of the self-assembly can be controlled. Further, even when the urea compound (1) is insoluble in the organic solvent, the organogel can be formed satisfactorily by mixing an inorganic salt or an inorganic ion within the above-mentioned range. It should be noted that the molar equivalent refers to a value derived by dividing the number of moles of an inorganic salt or an inorganic ion with the number of moles of the urea compound (1).

Any method may be employed as a mixing method as long as it is a method to dissolve the urea compound (1) in an organic solvent or to uniformly disperse the urea compound (1) in an organic solvent, and thus a known mixing method can be used.

The irradiation step is a step to irradiate an ultrasonic wave onto the aforementioned mixture and thereby to gelate the aforementioned mixture.

As for the conditions for the ultrasonic irradiation, any ultrasonic intensity and processing time sufficient to enable the aforementioned mixture to gelate may be used. For example, the rated output per unit area of the ultrasonic oscillator is preferably within the range from 0.2 to 0.5 W/cm$^2$, and more preferably within the range from 0.3 to 0.4 W/cm$^2$. The oscillation frequency of the ultrasonic oscillator is preferably within the range from 30 to 100 kHz, and more preferably within the range from 40 to 60 kHz. Further, the processing time is preferably from one minute to 24 hours, and more preferably from one hour to 12 hours.

As described above, since the urea compound (1) is highly symmetric, a design with high predictability due to the groups $X_1$, $X_2$ and $X_3$ in general formula (1) is possible. In addition, the urea compound (1) is capable of gelating a wide variety of organic solvents in a low concentration and forming organogels. Further, by adding an inorganic salt or an inorganic ion, the minimum gelation concentration of the urea compound (1) can be reduced, and the formation of organogels can be conducted at lower concentrations.

Due to the addition of an inorganic salt or an inorganic ion to the urea compound (I) of the present invention, the urea compound (1) mixes with this inorganic salt or inorganic ion and forms a self-assembly. By selecting the inorganic salt or inorganic ion to be added, the shape and size of the self-assembly can be controlled to selectively obtain any self-assembly. For this reason, it is possible to appropriately control the self-assembly and to adjust the function of the organogel in each of the case where a three-dimensional network structure is required and the case where the increase of a spherical surface area is expected.

In the organogel that uses the urea compound (1), it is thought that the hydrogen atom and oxygen atom in a urea group form hydrogen bonds with the hydrogen atom or oxygen atom in another urea group to form, for example, a fiber self-assembly, and these formed self-assemblies further foam a three-dimensional network structure. In addition, since the minimum gelation concentration of the urea compound (1) reduces by adding an inorganic salt or an inorganic ion, it can be assumed that inorganic ions are present in the bonds between the urea groups. Additionally, as described above, the effects of adding an inorganic salt or an inorganic ion differ depending on the type of organic solvent to be combined. By using the urea compound (1) that responds to the addition of such an inorganic salt or an inorganic ion, structure of the self-assembly can be controlled with high predictability and various functions can be given to the formed organogel.

In many cases, gels are formed by the external stimuli such as heat and ultraviolet rays. In contrast, in the present invention, organogels can be easily formed through the ultrasonic irradiation by using the urea compound (1). Therefore, the organogel that uses the urea compound (1) can be formed in the field of application in which cooling or ultraviolet irradiation has not been suitable in the past.

The urea compound of the present invention can be used as cosmetic products, drugs, bases in the field of agriculture, and formulations. Alternatively, the urea compound can also be used in a coating material, ink, lubricating oil, filler, or the like. In particular, when it is used as cosmetic products, drugs or bases of formulations for agriculture, it is useful as a sustained release base of component, such as a bioactive substance, and it is also useful as cosmetic products and drugs for eternal use, such as a moisturizer and wound dressing.

In addition, since the urea compound of the present invention undergoes sol-gel transformation due to the inorganic salt or inorganic ion which is present in the vicinity thereof, it is useful as a filler used in the civil engineering and construction, in the environmental cleanup or wastewater treatment for the uptake of metals or metal ions, and as a sensor or the like for detecting the presence of metals or metal ions. In addition, it is also useful as an organic reactant that uses the inside of a gel as a reaction site while exploiting the inorganic salt or inorganic ion which is mixed with the self-assembly.

EXAMPLES

Hereinafter, specific examples are described. However, the present invention is not limited to these specific examples.

Synthesis Example 1

Synthesis of Urea Compound A

A urea compound A represented by general formula (5) shown below was synthesized by: first synthesizing a nitro-form A represented by general formula (3) shown below by introducing nitrophenol into the 1st, 3rd, and 5th positions of phloroglucin represented by general formula (2) shown below (first step); then synthesizing an amine-form A represented by general formula (4) shown below by converting the nitro group of the nitro-form A to an amino group by the hydrogenation reaction (second step); and then introducing an urea group thereto by the reaction with an isocyanate (third step).

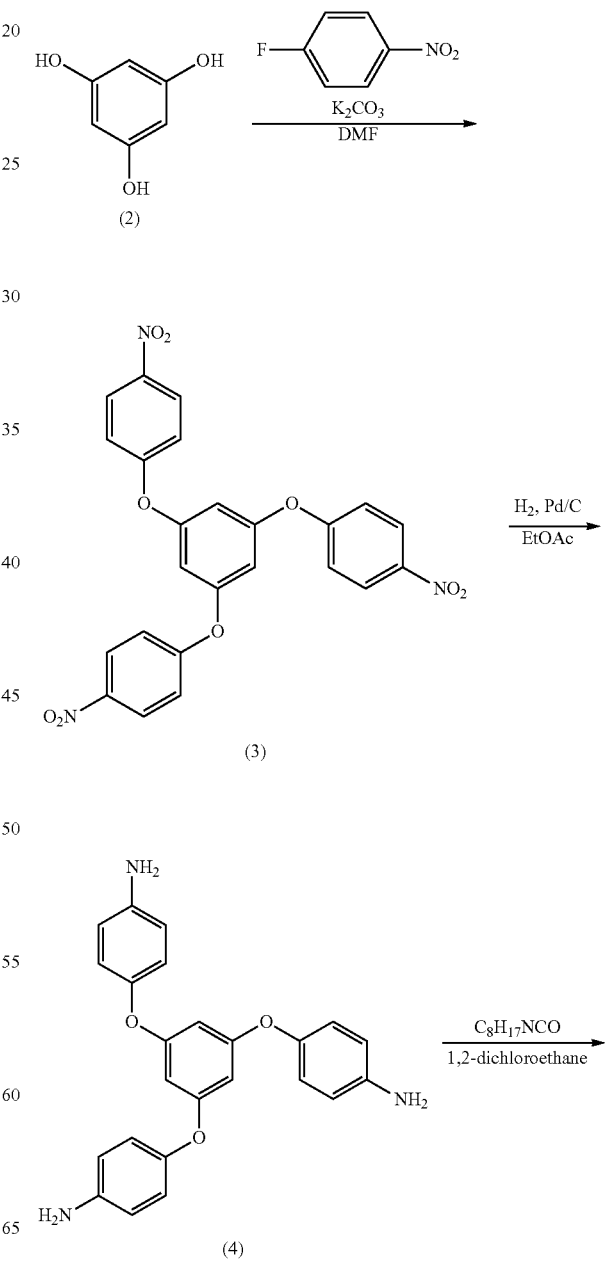

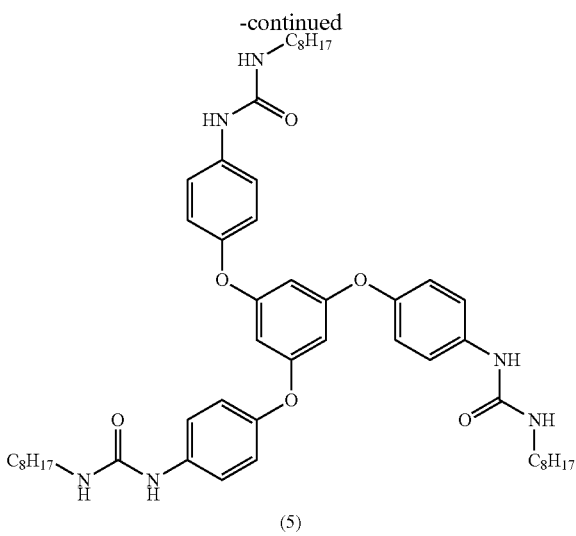

(5)

3.0 g (23.8 mmol) of phloroglucin represented by the above general formula (2) (manufactured by Tokyo Chemical Industry Co., Ltd.) and 65.8 g (476 mmol) of $K_2CO_3$ as an alkali catalyst were suspended in 240 mL of DMF serving as a first dispersion medium to prepare a suspension. 10 mL (94 mmol) of 4-fluoronitrobenzene (manufactured by Tokyo Chemical Industry Co., Ltd.) was added to the suspension to prepare a first dispersion, and the first dispersion was stirred for two days at 100° C. Thereafter, the first dispersion was cooled to room temperature, and $K_2CO_3$ was removed by filtration, and the first dispersion medium was evaporated by distillation under reduced pressure. The obtained residue was dissolved in dichloromethane serving as a collection medium for recovery and washed with water using a separatory funnel. After the washing, an aqueous phase was removed, and the resultant was washed once again using a separatory funnel by adding saturated saline thereto. Following the washing with saturated saline, an aqueous phase was removed, and a crude nitro-form obtained by evaporating the collection medium through distillation under reduced pressure was then purified by silica gel column chromatography (hexane:EtOAc=40:1 (volume ratio)) to obtain a nitro-form A (7.74 g) in the form of a yellow solid (first step).

The analysis results for the obtained nitro-form A by NMR were as follows.

$^1$H-NMR (600 MHz, CDCl$_3$, 25° C.): δ 6.65 (s, 3H), 7.13 (d, J=8.9 Hz, 6H), 8.26 (d, J=8.9 Hz, 6H)

$^{13}$C-NMR (150 MHz, CDCl$_3$, 25° C.): δ 108.0, 118.6, 126.5, 144.0, 158.2, 161.7

From the above results, it was confirmed that the nitro-form A was 1,3,5-tris(p-nitrophenoxy)benzene represented by the aforementioned general formula (3). Further, the yield of the nitro-form A was 67%. The yield is a percentage derived by dividing the number of moles for the obtained nitro-form A with the number of moles for the phloroglucin.

7.0 g (14.3 mmol) of the nitro-form A and 700 mg of Pd/C as a hydrogenation catalyst were suspended in EtOAc (140 mL) serving as a second dispersion medium to prepare a second dispersion. The second dispersion was stirred under a hydrogen atmosphere at room temperature for 16 hours. Following the stirring, Pd/C was removed by filtering the second dispersion, and the filtrate was concentrated using a rotary evaporator to yield a crude amine-form A. The obtained crude amine-form was purified by silica gel column chromatography (EtOAc) to yield an amine-form A (5.43 g) in the form of a brown solid (second step).

The analysis results for the obtained amine-form A by NMR were as follows.

$^1$H-NMR (600 MHz, CDCl$_3$, 25° C.): δ 6.15 (s, 3H), 6.64 (t, J=8.2 Hz, 6H), 6.84 (d, J=8.2 Hz, 6H)

$^{13}$C-NMR (600 MHz, CDCl$_3$, 25° C.): δ 100.3, 116.5, 121.5, 143.2, 148.1, 161.1

From the above results, it was confirmed that the amine-form A was 1,3,5-tris(p-aminophenoxy)benzene represented by the aforementioned general formula (4). Further, the yield of the amine-form A was 95%. The yield is a percentage derived by dividing the number of moles for the obtained amine-form A with the number of moles for the nitro-form A.

1.0 g (2.50 mmol) of the amine-form A was dissolved in 1,2-dichloroethane (50 mL), and 2.0 mL (11.3 mmol) of octyl isocyanate (manufactured by Wako Pure Chemical Industries, Ltd.) as an isocyanate was further added thereto to prepare a third dispersion A. After stirring at room temperature for one hour, the third dispersion A was heated and refluxed at 83° C. for 21 hours. Following the heating and refluxing, the third dispersion A was left standing to cool to room temperature. Then, the precipitated solid was separated by suction filtration, and the separated solid was washed with hexane and dichloromethane to yield a urea compound A (7.87 g) in the form of a skin color solid (third step).

The analysis results for the obtained urea compound A by NMR were as follows.

$^1$H-NMR (600 MHz, DMSO-d$_6$, 25° C.): δ 0.84 (t, J=6.9 Hz, 9H), 1.26-1.41 (m, 36H), 3.05 (dt, J=2.5, 6.5 Hz, 6H), 6.06-6.08 (m, 6H), 6.94 (d, J=8.9 Hz, 6H), 7.37 (d, J=8.9 Hz, 6H), 8.42 (s, 3H)

$^{13}$C-NMR (600 MHz, DMSO-d$_6$, 25° C.): δ 13.9, 22.1, 26.4, 28.7, 28.8, 28.8, 29.7, 31.2, 99.9, 119.0, 120.2, 137.3, 148.6, 155.2, 160.1

From the above results, it was confirmed that the urea compound A was a urea compound represented by the aforementioned general formula (5). Further, the yield of the urea compound A was 86%. The yield is a percentage derived by dividing the number of moles for the obtained urea compound A with the number of moles for the amine-form A.

Synthesis Example 2

Synthesis of Urea Compound B

<First Step>

200 mg (0.5 mmol) of the amine-form A obtained in Synthesis Example 1 was dissolved in 1,2-dichloroethane (10 mL) serving as a third dispersion medium, and 0.18 mL (1.66 mmol) of phenyl isocyanate (manufactured by Tokyo Chemical Industry Co., Ltd.) as an isocyanate was further added thereto to prepare a third dispersion B. After stirring the third dispersion B at room temperature for 10 hours, the precipitated solid was separated by suction filtration, and the separated solid was washed with hexane to yield a urea compound B (388 mg) in the form of a white solid (third step).

The analysis results for the obtained urea compound B by NMR were as follows.

$^1$H-NMR (600 MHz, DMSO-d$_6$, 25° C.): δ 6.95 (t, J=7.6 Hz, 3H), 7.03 (d, J=8.9 Hz, 6H), 7.26 (t, J=7.9 Hz, 6H), 7.43 (d, J=8.2 Hz, 6H), 7.46 (d, J=8.9 Hz, 6H), 8.64 (s, 3H), 8.70 (s, 3H)

$^{13}$C-NMR (600 MHz, DMSO-d$_6$, 25° C.): δ 100.4, 118.2, 119.8, 120.3, 121.8, 128.8, 136.3, 139.7, 149.5, 152.6, 160.0

From the above results, it was confirmed that the urea compound B was a urea compound represented by general formula (6) shown below. Further, the yield of the urea compound B was 89%. The yield is a percentage derived by dividing the number of moles for the obtained urea compound B with the number of moles for the amine-form A.

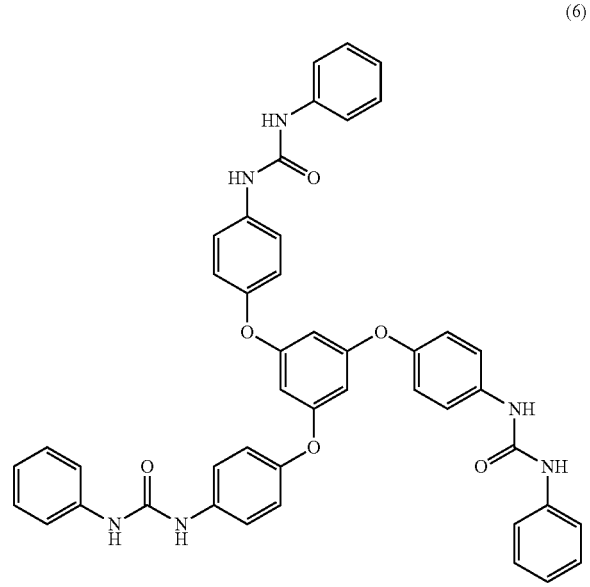

(6)

was 3 mmol/L, 4 mmol/L, 5 mmol/L, 10 mmol/L, 15 mmol/L or 25 mmol/L, and an ultrasonic wave was irradiated using an ultrasonic cleaning machine (B2510J-DTH, manufactured by Branson Ultrasonics Division of Emerson Japan, Ltd.) with a frequency of 42 kHz and an output of 0.39 W/cm$^2$. Following the ultrasonic irradiation, the inside of the screw tube was visually observed to assess the gel formation. As for the assessment, when the screw tube was inverted, the samples in which an organic solvent did not flow down were assessed as "satisfactory", and the samples in which the formation of precipitates or the separation of liquid layers was observed was assessed as "poor", in terms of gel formation. Regarding the samples that were assessed as "satisfactory" in terms of gel formation in this manner, the minimum gelation concentration of the urea compound A with respect to various organic solvents was determined. The results are shown in Table 1.

Examples 2 to 7, 9 to 12, 14 to 19 and 21 to 24

The minimum gelation concentration of the urea compound A necessary for gelating various organic solvents was determined in the same manner as in Example 1, with the exception that the inorganic salt indicated in Table 1 was added in an equimolar amount to the urea compound A. The results are shown in Table 1.

TABLE 1

| Example | Organic solvent | Inorganic salt (Type) | Inorganic salt concentration (mmol) | Ultrasonic treatment (h) | Minimum gelation concentration of urea compound A | |
|---|---|---|---|---|---|---|
| | | | | | (mmol) | (% by mass) |
| 1 | Methanol | — | — | 4 | 5 | 0.55 |
| 2 | Methanol | $CuCl_2$ | 3 | 4 | 3 | 0.33 |
| 3 | Methanol | $MgCl_2$ | 3 | 4 | 3 | 0.33 |
| 4 | Methanol | $MgBr_2$ | 3 | 4 | 3 | 0.33 |
| 5 | Methanol | $La(Otf)_3$ | 4 | 4 | 4 | 0.44 |
| 6 | Methanol | $Y(NO_3)_3$ | 3 | 4 | 3 | 0.33 |
| 7 | Methanol | NaI | 3 | 4 | 3 | 0.33 |
| 8 | Acetone | — | — | 4 | 10 | 1.1 |
| 9 | Acetone | CuBr | 10 | 4 | 10 | 1.1 |
| 10 | Acetone | $MgCl_2$ | 10 | 4 | 10 | 1.1 |
| 11 | Acetone | CsBr | 10 | 4 | 10 | 1.1 |
| 12 | Acetone | $La(Otf)_3$ | 10 | 4 | 10 | 1.1 |
| 13 | Chloroform | — | — | 4 | 15 | 0.87 |
| 14 | Chloroform | $CuBr_2$ | 3 | 4 | 3 | 0.17 |
| 15 | Chloroform | $MgCl_2$ | 10 | 4 | 10 | 0.58 |
| 16 | Chloroform | CsBr | 10 | 4 | 10 | 0.58 |
| 17 | Chloroform | $LaCl_3$ | 10 | 4 | 10 | 0.58 |
| 18 | Chloroform | $Y(NO_3)_3$ | 5 | 4 | 5 | 0.29 |
| 19 | Chloroform | NaI | 10 | 4 | 10 | 0.58 |
| 20 | Ethyl acetate | — | — | 4 | 15 | 1.44 |
| 21 | Ethyl acetate | $La(Otf)_3$ | 5 | 4 | 5 | 0.48 |
| 22 | Dichloromethane | $BiCl_3$ | 15 | 4 | 15 | 0.96 |
| 23 | Dichloromethane | $MgBr_2$ | 15 | 5.5 | 15 | 0.96 |
| 24 | Dichloromethane | $CuCl_2$ | 15 | 5.5 | 15 | 0.96 |

As shown in Synthesis Examples 1 and 2, it became clear that an intended urea compound can be obtained through the first to third steps by using phloroglucin as a starting material.

Examples 1, 8, 13, 20

1 mL of an organic solvent shown in Table 1 was added in a screw tube, and the urea compound A obtained in Synthesis Example 1 was added thereto so that the concentration thereof It became apparent as seen from the results shown in Table 1 that the urea compound A was capable of gelating methanol, acetone, chloroform and ethyl acetate. In addition, it became evident from the results of Examples 1, 8, 13 and 20 that the minimum gelation concentration of the urea compound A was as low as 0.55 to 1.44% by mass.

When methanol was used as an organic solvent, the minimum gelation concentration of the urea compound A was 5 mmol/L in Example 1 where no inorganic salt was added, whereas a reduction in the minimum gelation concentration was observed in Examples 2 to 7 where an inorganic salt was added. When chloroform was used as an organic solvent, the minimum gelation concentration of the urea compound A was 15 mmol/L in Example 13 where no inorganic salt was added. On the other hand, the minimum gelation concentration of the urea compound A was 3 to 10 mmol/L in Examples 14 to 19 where an inorganic salt was added. In particular, in Example 14 where $CuBr_2$ was added as an inorganic salt, the minimum gelation concentration of the urea compound A was 3 mmol/L (0.17% by mass), and the minimum gelation concentration of the urea compound A was 5 mmol/L (0.29% by mass) in Example 18 where $Y(NO_3)_3$ was added, and thus a marked reduction in the minimum gelation concentration was observed. When ethyl acetate was used as an organic solvent, the minimum gelation concentration of the urea compound A was 15 mmol/L in Example 20 where no inorganic salt was added. The minimum gelation concentration of the urea compound A was 5 mmol/L (0.48% by mass) in Example 21 where an inorganic salt was added, and thus a significant reduction in the minimum gelation concentration was observed due to the addition of an inorganic salt.

When dichloromethane was used as an organic solvent, the urea compound A was insoluble in dichloromethane and did not gelate even when an ultrasonic wave was irradiated in those cases where no inorganic salt was added. However, as in Examples 22 to 24, it became clear that the urea compound A forms gels by adding an inorganic salt and irradiating an ultrasonic wave.

As described above, it became clear that the urea compound A forms gels in a wide variety of organic solvents. In addition, it became clear that the minimum gelation concentration of the urea compound A reduces by selecting an inorganic salt that is suitable for an organic solvent. Further, it became apparent that the urea compound A is capable of forming gels at an extremely low concentration of 0.5% by mass or less by selecting an appropriate inorganic salt. Moreover, it became apparent that the urea compound A is capable of gelating an even wider variety of organic solvents by adding an appropriate inorganic salt.

Example 25

0.5 mL of chloroform was added in a screw tube as an organic solvent, and the urea compound A obtained in Synthesis Example 1 was added thereto so that the concentration thereof was 15 mmol/L, and an ultrasonic wave was irradiated for 4 hours to form a gel using an ultrasonic cleaning machine (B2510J-DTH, manufactured by Branson Ultrasonics Division of Emerson Japan, Ltd.) with a frequency of 42 kHz and an output of 0.39 W/cm². With respect to the obtained gel, the self-assembly that formed the gel was observed by using a scanning electron microscope (SEM) (magnification: ×2,700). An SEM image is shown in FIG. 1.

Example 26

Figure 2:
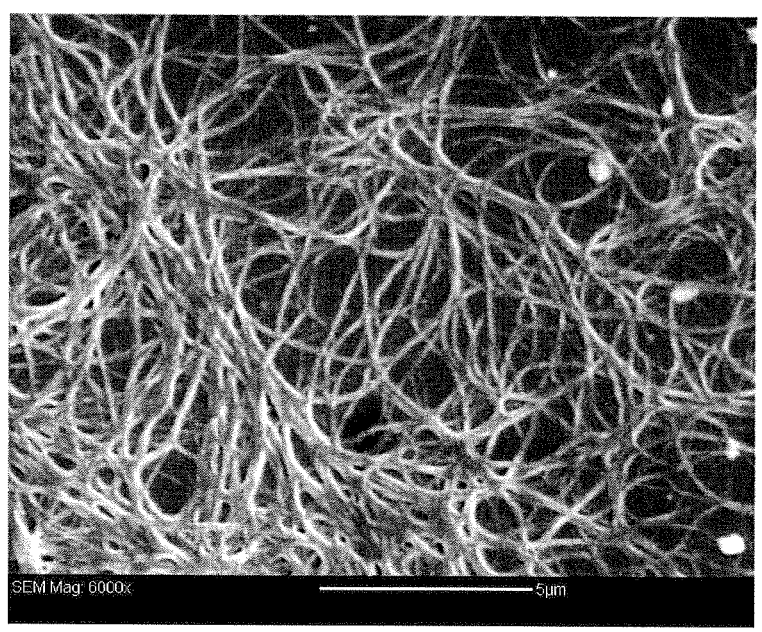
FIG. 2 is an SEM image of a gel obtained in Example 26.

A gel was formed in the same manner as in Example 25 with the exception that the concentration of the urea compound A was adjusted to 5 mmol/L and 5 mmol/L of CuCl was added, and SEM observation was conducted (magnification: ×6,000). An SEM image is shown in FIG. 2.

Example 27

Figure 3:
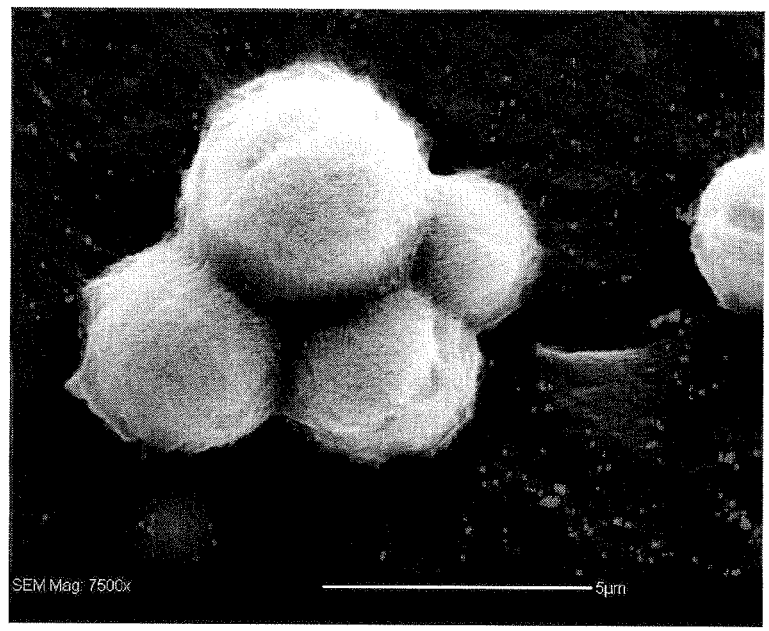
FIG. 3 is an SEM image of a gel obtained in Example 27.

A gel was formed in the same manner as in Example 25 with the exception that the concentration of the urea compound A was adjusted to 10 mmol/L and 10 mmol/L of CsBr was added, and SEM observation was conducted (magnification: ×7,500). An SEM image is shown in FIG. 3.

Example 28

Figure 4:
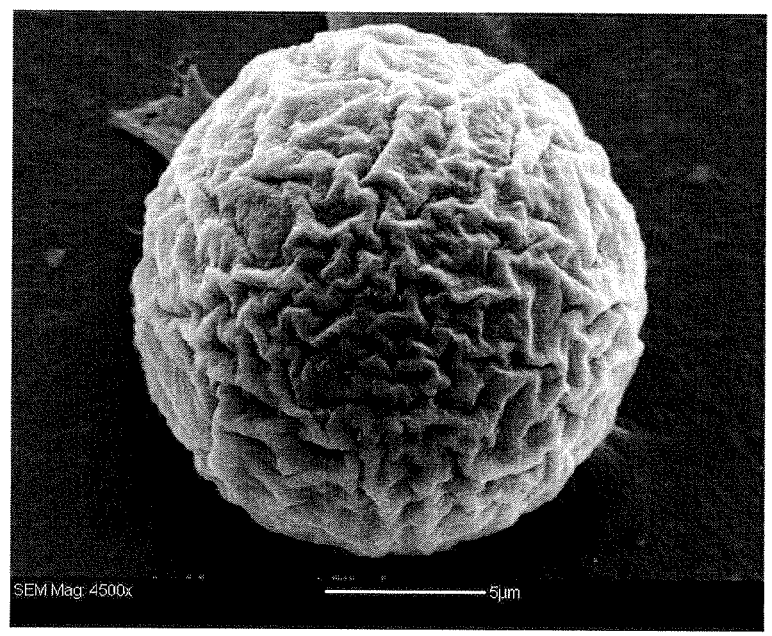
FIG. 4 is an SEM image of a gel obtained in Example 28.

A partial gel was formed in the same manner as in Example 25 with the exception that the concentration of the urea compound A was adjusted to 10 mmol/L and 10 mmol/L of $Y(NO_3)_3$ was added, and SEM observation was conducted (magnification: ×4,500). An SEM image is shown in FIG. 4.

In Example 25, as shown in FIG. 1, a fiber self-assembly which was a structural feature of a general gel was observed. Also in Example 26, a fiber self-assembly which was a structural feature of a gel was observed. On the other hand, in Example 27, a self-assembly in which particulate assemblies were aggregated was observed as shown in FIG. 3, and also in Example 28, a particulate self-assembly was observed as shown in FIG. 4. From these observation results, it became clear that the self-assembly can be controlled to form a desired shape by selecting the type of an organic solvent, the concentration of the urea compound A, and the type and concentration of an inorganic salt.

The invention claimed is:

1. A urea compound represented by general formula (I) shown below:

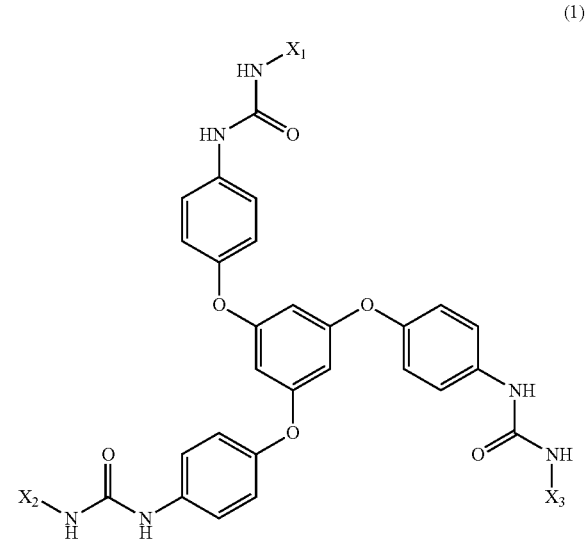

(1)

wherein each of $X_1$, $X_2$ and $X_3$ independently represents a hydrogen atom, an alkyl group or an aryl group; and the aryl group may have one or more functional groups selected from the group consisting of halogen groups, alkyl groups and alkoxy groups.

2. The urea compound according to claim 1, wherein each of $X_1$, $X_2$, and $X_3$ independently represents hydrogen, or a linear or branched alkyl group of 1 to 22 of carbon atoms.

3. The urea compound according to claim 1, wherein each of $X_1$, $X_2$, and $X_3$ independently represents a liner or branched alkyl group of 8 to 16 carbon atoms.

4. A self-assembly which is formed by self-assembling of the urea compound of claim 1.

5. The self-assembly according to claim 4 comprising an inorganic salt or an inorganic ion.

6. The self-assembly according to claim 5, wherein the inorganic salt is at least one kind of salt selected from the group consisting of an yttrium salt, a cesium salt, a lanthanum salt, a copper salt, a magnesium salt and an ytterbium salt.

7. The self-assembly according to claim 5, wherein the inorganic ion is at least one kind of ion selected from the group consisting of an yttrium ion, a cesium ion, a lanthanum ion, a copper ion, a magnesium ion and an ytterbium ion.

8. A particulate self-assembly which is formed by mixing the urea compound of claim 1 with an yttrium salt, a cesium salt, an yttrium ion or a cesium ion.

9. A fiber self-assembly which is formed by mixing the urea compound of claim 1 with a copper salt, a lanthanum salt, a magnesium salt, an ytterbium salt, a copper ion, a lanthanum ion, a magnesium ion or an ytterbium ion.

10. An organogel comprising the urea compound of claim 1 and an organic solvent.

11. An organogel comprising the self-assembly of claim 4 and an organic solvent.

12. An organogel comprising the particulate self-assembly of claim 8 and an organic solvent.

13. An organogel comprising the fiber self-assembly of claim 9 and an organic solvent.

14. A method for producing an organogel comprising: a mixing step of mixing the urea compound of claim 1 and an organic solvent to obtain a mixture; and an irradiation step of irradiating an ultrasonic wave onto the mixture.

15. The method for producing an organogel according to claim 14, wherein an inorganic salt or an inorganic ion is further mixed in the mixing step.

* * * * *